United States Patent [19]

Storz

[11] Patent Number: 5,460,615

[45] Date of Patent: Oct. 24, 1995

[54] TROCAR SLEEVE

[76] Inventor: Karl Storz, Auf dem Schildrain 39, D-78532 Tuttlingen, Germany

[21] Appl. No.: 156,615

[22] Filed: Nov. 23, 1993

[30] Foreign Application Priority Data

Nov. 24, 1992 [DE] Germany .......................... 42 39 403.1

[51] Int. Cl.[6] .......................... A61M 5/00; A61M 25/00
[52] U.S. Cl. .......................... 604/167; 137/849; 604/256
[58] Field of Search .......................... 606/185, 184, 606/167; 604/27, 33, 21, 164–167, 256, 96–103; 137/846, 849

[56] References Cited

U.S. PATENT DOCUMENTS

| | | | |
|---|---|---|---|
| 4,929,235 | 5/1990 | Merry et al. .......................... | 604/167 |
| 5,104,383 | 4/1992 | Shichman .......................... | 604/256 X |
| 5,188,605 | 2/1993 | Sleep .......................... | 604/167 X |
| 5,205,831 | 4/1993 | Ryan et al. .......................... | 604/167 |
| 5,242,389 | 9/1993 | Schrader et al. .......................... | 604/167 X |
| 5,256,147 | 10/1993 | Vidal et al. .......................... | 604/158 |

*Primary Examiner*—Stephen C. Pellegrino
*Assistant Examiner*—Nancy Mulcare
*Attorney, Agent, or Firm*—Donald D. Mon

[57] ABSTRACT

A trocar sleeve for endoscopic operations has valve means and seal means on the end of the trocar sleeve remote from the patient. In addition to a seal with a large diameter, at least one support element for a further seal with a smaller diameter is provided.

7 Claims, 2 Drawing Sheets

TROCAR SLEEVE

The invention relates to a trocar sleeve for endoscopic operations, with valve means and a seal on the end of the trocar sleeve remote from the patient, through which sleeve instruments can be guided.

German Published Application 40 21 023 discloses a trocar with a trocar sleeve that is sealed by the trocar mandrel. The trocar mandrel can be replaced by a variety of instruments, including those with different thicknesses.

German Utility Model 71 45 806 discloses a trocar provided with an insertion sleeve into which sleeve two operating instruments are arranged. The insertion sleeve has a membrane seal with two bores, spaced apart for receiving operating instruments.

In a trocar known from German Utility Model 75 13 492, it is easily possible to undo a connection between a casing tube and a trocar sleeve, so an air channel can easily be cleaned.

Depending on the type of intervention, instruments of various thicknesses are used, each of which must be manipulated in a gas-tight manner. It is therefore necessary to provide a seal, usually made of rubber, in particular in the form of sealing caps which have various bores that correspond to the diameter or thickness of the particular instrument to be introduced. For example, if a sealing cap is used that is designed for use with an instrument having a relatively large outside diameter, the corresponding opening in the sealing cap has a relatively large diameter. If an instrument with a considerably smaller diameter is pushed through such a seal, sealing between the seal and the instrument would no longer be ensured. A variety of seals or rubber caps with various bores must therefore be kept on hand, so they can be exchanged if necessary.

This is disruptive for the operator, and time-consuming.

It is therefore object of the present invention to provide a trocar sleeve with a seal which can be exchanged quickly and easily.

According to the invention, the object is achieved by the fact that the trocar sleeve has, in addition to a perforated seal with a large diameter, at least one support element for a further seal with a smaller diameter.

Due to the provisions of at least one support element for a further seal with a smaller diameter, a procedure which is to perform in a simple and rapid manner can be used when necessary to bring the seal with a smaller diameter into position.

Because the support element is present directly on the trocar sleeve, the further seal does not have to be picked up from a distant location at which it was disposed previously, and installed onto the trocar sleeve. The replacement or exchange procedure can be performed in seconds, and does not require close attention; i.e. attention can continue to be directed, for example, to the endoscopic procedure.

In a further embodiment of the invention, the at least one support element is connected to the trocar sleeve by means of an articulation.

The considerable advantage of this feature is that the exchange process can be performed by a simple pivoting procedure, which can be performed easily, quickly, and reliably.

In a further embodiment of the invention, the articulation is arranged on a rigid holder, which in a particularly advantageous fashion is arranged radially extending from the trocar sleeve.

The advantage of these features is that if the seal disposed on the support element is not needed, the support element is located radially distant from the outer side of the trocar sleeve, and thus does not interfere with the manipulations in the trocar sleeve, which are performed substantially in axial direction. Thus if necessary, a plurality of radially distant support elements can also be used in a space-saving manner; they are then suitably spaced apart circumferentially. For example, if in addition to one instrument with a relatively large diameter, two further instruments with smaller diameters which differ from one another are used, it is also possible to provide two support elements, spaced apart for example at angles of 90° to 120° around the circumference, which can then each be pivoted in and brought into position.

In a further embodiment of the invention, the support element has a connection piece by means of which it can be inserted into the passthrough opening in the large-diameter seal.

The considerable advantage of this feature is that by means of the connection piece, the support element can be inserted into the large opening of the seal easily and with a tight fit.

In a further embodiment of the invention, the valve means is sealed by means of a bayonet fastener, the valve means having a bayonet guide into which a cover can be twisted. It is especially preferred in this connection for the cover to support the at least one support element.

The advantage of this feature is first that the valve means can very easily be opened for cleaning, and second that by a simple movement of the bayonet fastener, a cover with a different support element can also be inserted if necessary. As a result, trocar sleeves of identical size with different covers, which then have correspondingly different support elements, can be made available.

It is understood that the features mentioned above and those yet to be explained below can be used not only in the combinations indicated, but also in other combinations or in isolation, without leaving the context of the invention.

The invention will be described in greater detail and explained below with reference to several selected exemplary embodiments, in conjunction with the drawings, in which.

Figure 1:
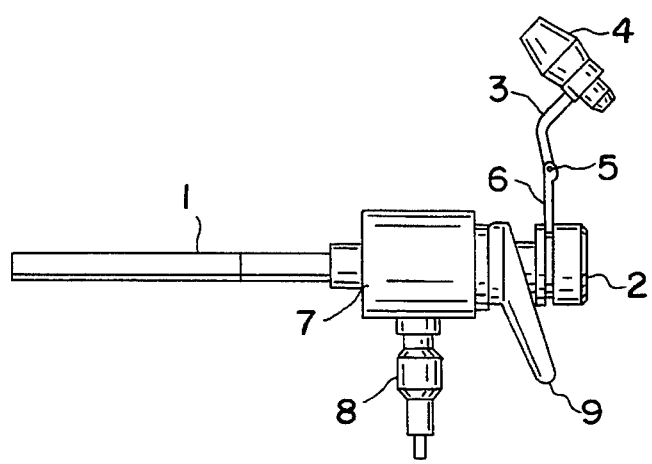
FIG. 1 shows a side view of a first exemplary embodiment of a trocar sleeve according to the invention, without an instrument.

FIG. 1 shows a trocar sleeve 1 at one end of which valve means 7 is arranged. The valve means 7 comprise a flap valve allowing the passage of instruments with various thicknesses. A more detailed description of such valve means, known in the art per se, is done in conjunction with the embodiment of FIGS. 4 to 7.

A connection 8 for a rinsing fluid or for the passage of air projects radially from the valve means 7. The connection 8 can be opened or closed by means of a stopcock (not characterized further here). Connections of this kind with various functions are also known in this art, and therefore do not need to be individually depicted further.

A lever 9 for switching the valve means 7 is arranged at the end of the valve means 7 remote from the patient.

The detailed operation and configuration of the valve means are also described in conjunction with the embodiment according to FIGS. 4 to 7.

Figure 2:
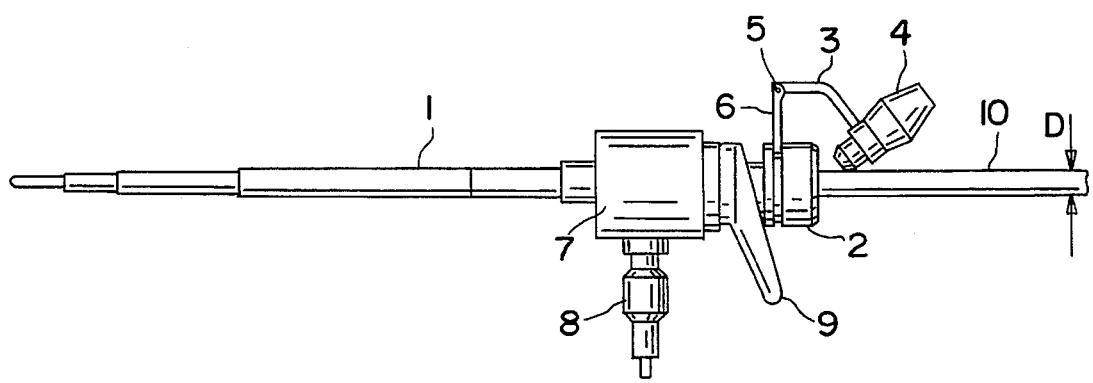
FIG. 2 shows a view corresponding to FIG. 1, but after the introduction of a large-diameter operating instrument.

A cap-shaped rubber seal 2 is provided at the end of the trocar sleeve 1 remote from the patient, said seal 2 is intended to allow passage of an instrument 10 with a large diameter D, as it is evident from FIG. 2.

In the region of the rubber seal 2 a holder 6 is provided that is arranged radially, i.e. extending at an angle to the trocar sleeve 1. At the outer end of the holder 6 an articulation 5 is provided on which a support element 3 is arranged, supporting a sealing cap 4 allowing a passage of an operating instrument 11 with a small diameter d, as shown in FIG. 3.

FIG. 1 shows a position in which the support element 3 with the sealing cap 4 is pivoted radially about the articulation 5 to point outwardly.

It is evident from FIG. 2 that an operating instrument 10 with a relatively large diameter D is introduced into the trocar sleeve. In the embodiment shown, the diameter D is approximately 5 mm. The operating instrument 10 thus extends in a sealed manner through the rubber seal 2 i.e. through the opening present therein. In FIG. 2, the sealing cap 4 is pivoted along with the support element 3 about the articulation 5; manipulation of the operating instrument 10, which is slid in and out axially, is not thereby impaired.

Figure 3:
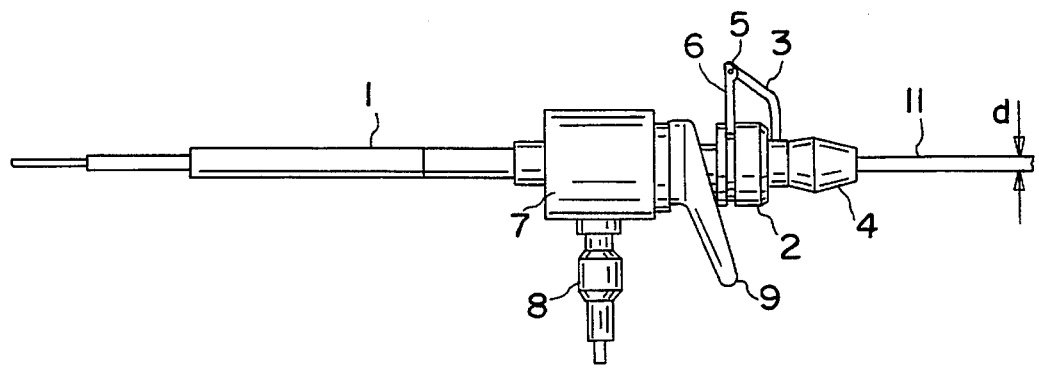
FIG. 3 shows a depiction corresponding to the depiction of FIG. 2, but after insertion of an operating instrument with a smaller diameter.

FIG. 3 shows a situation in which the support element 3 is pivoted and a projecting tube-like connection piece of the support element engages into the opening of the rubber seal 2. The sealing cap 4, and its smaller-diameter passthrough opening sits coaxially on the trocar sleeve. FIG. 3 thus shows how an operating instrument 11 with a smaller diameter d, in this case for example 3 mm, is inserted into the trocar sleeve.

It is not necessary for the support element 3 to penetrate with the tube-shaped projection into the rubber seal 2; it is sufficient if it simply rests against the rubber seal 2.

It is obvious that the process of pivoting from the position shown in FIG. 1 via the one shown in FIG. 2 to the pivoted position of the support element 3 shown in FIG. 3 is very simple, and can be performed in seconds.

The inverse procedure can be performed correspondingly i.e. once the operating instrument 11 has been withdrawn from the position shown in FIG. 3, the support element 3 can be pivoted back into the position shown in FIG. 1 with a simple pivoting motion, and an operating instrument 10 with a larger diameter can then be reinserted through the sealing cap 2.

FIGS. 1 to 3 show a single support element 3, but it is also possible to provide, for example, two or even a plurality of support elements distributed circumferentially. Provision can also be made to design the articulation 5 in such a way that it moves relatively stiffly, so that a support element pivoted aside remains in its particular position, and does not swing back under its own weight if the trocar sleeve is in an oblique or tilted position. On the other hand, the stiffness is only such that the support element 3 can still easily be moved by hand.

It is possible, alternatively, first to remove the rubber seal 2, which can be done by pulling it off, and then to pivote the support element appropriately. Care must then be taken that the support element rests in a sealed manner against the valve means 7.

FIGS. 4 to 7 show a further embodiment whose design in terms of its essential constituents, especially with respect to the support element 3 according to the invention, is identical to that of the embodiment described previously.

Figure 4:
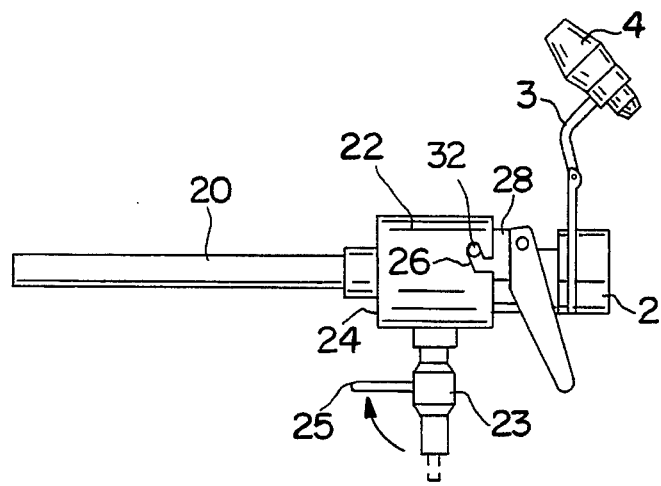
FIG. 4 shows a side view, corresponding to the depiction of FIG. 1, of a further exemplary embodiment with a bayonet fastener.
Figure 5:
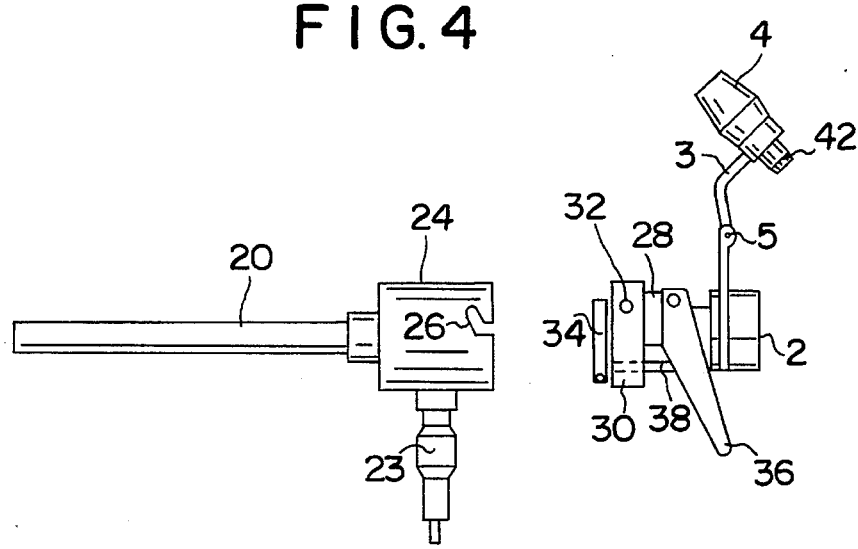
FIG. 5 shows a depiction corresponding to FIG. 4, in which a cover part of the bayonet fastener has been removed.

The trocar sleeve 20 shown in FIGS. 4 and 5 is provided with valve means 22 from which a connection 23 projects radially. A pivoting lever 25 is used to open and close the connection 23.

The valve means 22 has a housing 24 into the end of which, remote from the patient, a bayonet guide 26 is recessed.

At the end remote from the patient, the housing 24 is closed by a cover 28 that is provided, at the end facing the housing, with a plate 30 whose outside diameter corresponds approximately to the inside diameter of the hollow cylindrical housing 24.

Projecting radially from the plate 30 is a pin 32 that is provided to engage with the bayonet guide 26, thereby providing a bayonet closure.

On the end facing the housing 24, the plate 33 is provided with a valve flap 34 that can be opened in various ways.

Figure 6:
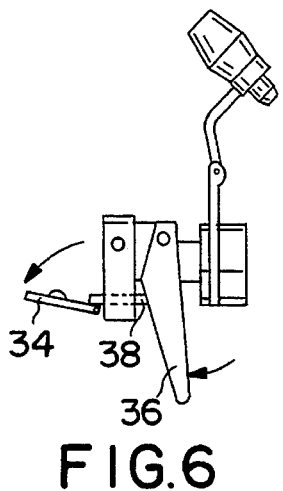
FIG. 6 shows the removed cover part visible in FIG. 5, in a functioning position with the valve flap open.

It is evident from FIG. 6 that the valve flap 34 can be opened by pivoting a pivoting lever 36 about its pivot axis, as indicated in FIG. 6 by an arrow; an axially oriented plunger, connected to the pivoting lever 36, opens the valve means 34.

Figure 7:
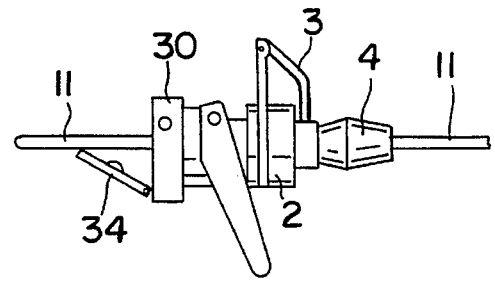
FIG. 7 shows a depiction of the cover part of the trocar sleeve alone, comparable to the functioning position of FIG. 3.

It is evident from FIG. 7 that the valve flap 34 can also be opened when an operating instrument 11 is slid through (this is equally true for a larger-diameter instrument 10).

The pivoted position of the support element 3 shown in FIG. 7 corresponds to the position shown in FIG. 3, i.e. a projecting tube-like connection piece 42 is pushed into the sealing cap 4 so that the sealing cap 4, or its passthrough opening, is then aligned coaxially with the passthrough opening of the rubber seal 2.

What is claimed is:

1. A trocar sleeve for endoscopic operations, comprising:
   a trocar sleeve through which sleeve instruments can be guided,
   valve means for closing a passage in said trocar sleeve,
   first seal means at one end of said trocar sleeve, said end being remote from a patient to be treated with said trocar sleeve, said first seal means comprising a fixedly mounted perforated seal with a larger diameter opening, and at least one support element supporting a second seal having a smaller diameter opening, said second support element being connected to said trocar sleeve by emans of an articulation enabling the transfer of the smaller diameter opening seal by a swivelling movement from a first position remote from the trocar sleeve passage, to a second position in coaxial alignment of the smaller diameter opening with the larger diameter opening, said support element sealing with said first seal means when said articulation is in said second position.

2. The trocar sleeve according to claim 1, wherein said articulation is arranged on a rigid holder.

3. The trocar sleeve according to claim 2, wherein said holder is arranged radially extending from the said trocar sleeve.

4. The trocar sleeve according to claim 1, wherein said support element has a tube-like connection piece by means of which piece it can be inserted into a passthrough opening in the large-diameter seal.

5. The trocar sleeve according to claim 1, wherein said valve means is provided with a bayonet closure.

6. The trocar sleeve according to claim 5, wherein said valve means comprises a housing having a bayonet guide, and said valve means further comprises a cover having a pin, said pin can be introduced into said bayonet guide in said housing of said valve means.

7. The trocar sleeve according to claim 6, wherein said cover supports at least one support element.

* * * * *